(12) United States Patent
Nivala

(10) Patent No.: US 8,191,711 B2
(45) Date of Patent: *Jun. 5, 2012

(54) BEND AND PEEL TABLET PACKAGE

(75) Inventor: Michelle Nivala, St. Paul, MN (US)

(73) Assignee: Cima Labs Inc., Brooklyn Park, MN (US)

( * ) Notice: Subject to any disclaimer, the term of this patent is extended or adjusted under 35 U.S.C. 154(b) by 146 days.

This patent is subject to a terminal disclaimer.

(21) Appl. No.: 11/330,728

(22) Filed: Jan. 12, 2006

(65) Prior Publication Data

US 2006/0283759 A1 Dec. 21, 2006

Related U.S. Application Data

(60) Provisional application No. 60/644,393, filed on Jan. 14, 2005.

(51) Int. Cl.
*B65D 85/42* (2006.01)

(52) U.S. Cl. ............ 206/532; 206/528; 206/534.1

(58) Field of Classification Search .......... 206/532, 206/539, 469, 534.1, 538
See application file for complete search history.

(56) References Cited

U.S. PATENT DOCUMENTS

| | | | | |
|---|---|---|---|---|
| 3,811,564 A | * | 5/1974 | Braber ................. | 206/469 |
| 3,921,805 A | * | 11/1975 | Compere ................ | 206/532 |
| 3,924,746 A | * | 12/1975 | Haines ................. | 206/530 |
| 3,941,248 A | | 3/1976 | Moser et al. | |
| 4,011,949 A | * | 3/1977 | Braber et al. .......... | 206/532 |
| 4,158,411 A | | 6/1979 | Hall et al. | |
| 4,243,144 A | * | 1/1981 | Margulies .............. | 206/532 |
| 4,988,004 A | * | 1/1991 | Intini ................. | 206/532 |
| 5,046,618 A | * | 9/1991 | Wood .................. | 206/532 |
| 5,178,878 A | | 1/1993 | Wehling et al. | |
| 5,223,264 A | | 6/1993 | Wehling et al. | |
| 5,234,957 A | | 8/1993 | Mantelle | |
| 5,310,060 A | * | 5/1994 | Bitner et al. .......... | 206/532 |
| 5,325,968 A | * | 7/1994 | Sowden ................ | 206/532 |
| 5,758,774 A | | 6/1998 | Leblong | |
| 5,851,553 A | | 12/1998 | Myers et al. | |
| 5,878,888 A | * | 3/1999 | Faughey et al. ......... | 206/532 |
| 5,944,191 A | | 8/1999 | Ray et al. | |
| 6,047,829 A | | 4/2000 | Johnstone et al. | |
| 6,155,423 A | * | 12/2000 | Katzner et al. ......... | 206/531 |
| 6,230,893 B1 | | 5/2001 | Karow | |
| 6,752,272 B2 | | 6/2004 | Jones et al. | |

(Continued)

FOREIGN PATENT DOCUMENTS

WO 00/24647 5/2000

(Continued)

OTHER PUBLICATIONS

MeadWestvaco Healthcare Packaging Advertisement for shellpak Plastic Blister Housing.

(Continued)

*Primary Examiner* — J. Gregory Pickett
*Assistant Examiner* — Kaushikkumar Desai
(74) *Attorney, Agent, or Firm* — Cima Labs Inc.

(57) ABSTRACT

A blister package and method of removing a dosage form from a blister package are disclosed. In one embodiment, the blister package includes a unitary blister sheet and a unitary sheet of lidding material. The lidding sheet is peelably sealed to the blister sheet, and includes unsealed areas for facilitating the peeling of the lidding material from the blister sheet. The unsealed areas are preferably only accessible upon a bending of the blister package.

18 Claims, 4 Drawing Sheets

U.S. PATENT DOCUMENTS

| | | | |
|---|---|---|---|
| 6,761,910 B1 * | 7/2004 | Pettersson et al. | 424/489 |
| 7,093,716 B2 * | 8/2006 | Intini | 206/532 |
| 7,395,928 B2 * | 7/2008 | Bertsch et al. | 206/531 |
| 2003/0209461 A1 | 11/2003 | French et al. | |

FOREIGN PATENT DOCUMENTS

| | | |
|---|---|---|
| WO | 01/02265 | 1/2001 |

OTHER PUBLICATIONS

Alcan Packaging Presentation of CR Concepts F=1 for Cima Labs, May 15, 2002, 10 pgs.

U.S. Appl. No. 11/330,729, filed Jan. 12, 2006.

Eurasian Office Action issued on Aug. 20, 2008 in connection with corresponding Eurasian Application No. 200701512 (2007080080).

* cited by examiner

BEND AND PEEL TABLET PACKAGE

CROSS-REFERENCE TO RELATED APPLICATIONS

This application claims the benefit of the filing date of U.S. Provisional Patent Application No. 60/644,393 filed Jan. 14, 2005, the disclosure of which is hereby incorporated herein by reference

BACKGROUND OF THE INVENTION

Many people, as part of their daily routine, take various types of medication. Some may take several different types of pharmaceutical dosage forms in a given period. These pharmaceutical dosage forms may include pills, capsules, tablets, liquids and the like. As with many industries for which a tangible product is offered for sale, packaging is an issue. Often times, the manner in which a product is offered is a deciding factor in whether or not a purchase is made. This situation is no different in the pharmaceutical field. But other concerns may also drive the style of packaging in the pharmaceutical industry.

One packaging concern is the nature of the dosage form. Some tablets, for example, are frangible, friable or breakable (used synonymously). Such dosage forms may be easily damaged both during transport of the package and by a user upon opening. The disclosures of commonly assigned U.S. Pat. Nos. 5,178,878 and 5,223,264, which are hereby incorporated by reference herein, describe relatively soft tablets which are susceptible to this type of damage. Tablets which fall into this category tend to have a low hardness and high friability, and may include very soft tablets with a hardness below about 15 Newtons.

Standard dosage forms are typically packaged in blister packages, which are comprised of multi-layered sheets of material having pockets, blisters or wells for containing the dosage forms. One type of conventional blister packages includes packages having a foil layer through which a user of the package must push the tablet, thereby breaking the foil. An example of such a conventional blister package is shown in U.S. Pat. No. 4,158,411 to Hall et al., the disclosure of which is hereby incorporated by reference herein. While this type of package is sufficient for packaging standard dosage forms, packaging of frangible dosage forms in such a package would cause damage to the frangible dosage form when attempting to push it through the foil layer. These types of packages are also generally not child proof.

Another concern with the packaging of pharmaceutical dosage forms, whether they are frangible dosage forms or not, relates to safety. Child proof or child resistant packaging is often very desirable for the packaging of dosage forms. Clearly, a big concern with having medication in the home is the possibility of a child gaining access to it. On the other hand, child-proof packages may also be quite difficult to open by the elderly, handicapped or people in great pain. There needs to be a balance struck, therefore, between safety and ease of use. Packages that are more difficult for children to open than, for example, the elderly are therefore highly desirable. In addition, not all child proof packaging is the same. Packaging is often rated based on the number of children who can gain access to the drug in five minutes. One example of testing procedure standards for achieving these ratings is set forth in 16 C.F.R., and in particular §1700.00 through 1700.20 thereof.

Therefore, there exists a need for a dosage package, capable of housing both frangible and/or non-frangible dosage forms, which can be easily modified to provide varying designs ranging from extremely child proof designs to designs that are easily operable.

SUMMARY OF THE INVENTION

The packages of the invention are preferably blister packages that require bending in order to access an unsealed area of a lidding material sheet. Upon access of the unsealed area, a user can peel away the lidding material from a blister sheet, thereby exposing any dosage forms housed therein. In certain embodiments, the present invention relates to packages for housing frangible or friable pharmaceutical dosage forms. In other embodiments, the blister packages for friable dosage forms are child resistant. In others, the blister packages are useful for packaging non-frangible tablets.

A first aspect of the present invention is a blister package for housing dosage forms, both frangible and non-frangible. The package includes, a unitary blister sheet or "bottom" defining at least one unit package region, the at least one unit package region including a recess (used synonymously with bubble, blister and well) having an open top and a flange surrounding the recess. Each recess (in the case of more than one recess) may accommodate one or more dosage forms. The package also includes a unitary sheet of lidding material or "top" peelably sealed to the flanges. The blister sheet and the sheet of lidding material further define at least one unsealed area for facilitating peeling of the lidding material from the blister sheet so as to provide access to the recess. These unsealed areas are preferably only accessible by a user upon the bending of at least a portion of the blister sheet and/or the sheet of lidding material in the proximity of the unsealed area. It is noted that if the blister sheet and/or the sheet of lidding material is scored or perforated, they do not technically bend. However, for purposes of the present invention, the term bend will encompass the folding over of such an area. In a preferred embodiment, the bending of at least a portion of the blister sheet and/or the sheet of lidding material splits or forces separation of at least a portion of the unsealed lidding material along a score line, line of weakness or line of perforations, thus allowing access to the unsealed areas.

Another aspect of the present invention is another blister package for housing dosage forms, both frangible and non-frangible. The blister package according to this aspect includes a blister sheet including at least one recess having an open top and a flange surrounding the recess and a sheet of lidding material including perforations. The sheet of lidding material is peelably sealed to at least a portion of the flanges and defines at least one unsealed area between the blister sheet and the sheet of lidding material. In this embodiment, perforations are located along at least a portion of the at least one unsealed area and bending of the blister package in the proximity of the perforations allows for splitting or separation of the perforations and access of the at least one unsealed area.

Yet another aspect of the present invention is a method of removing a dosage form from a blister package. The method according to this aspect includes providing a blister package having a blister sheet and a sheet of lidding material, where the blister sheet and the sheet of lidding material define at least one unit package region including at least one recess and at least one inaccessible unsealed area. The method also includes the steps of bending at least a portion of the blister package to allow access of the otherwise inaccessible unsealed area, grasping at least a portion of the lidding material adjacent the unsealed area, peeling away at least a portion of the lidding material to reveal at least one dosage form disposed in the recess and removing the at least one dosage form.

In certain preferred embodiments, the blister package is constituted of materials and configured to retard access through ripping, tearing, chewing, puncture, and the like, especially by children too young to know better. Indeed, because of the very adaptable design of the packages of the present invention, it is possible to make packages which can cover a variety of degrees of child proofing.

In another preferred embodiment according to the present invention, the blister package is designed to reduce breakage of a frangible tablet housed therein. The frangible dosage forms disposed in each recess of the preferred blisters engages the walls of each recess so that the walls hold the dosage form away from the bottom of the recess and adjacent the lidding material. This aspect protects the dosage form from damage by preventing shifting of the dosage form during transport. An empty space between each dosage form and the bottom of the recess in which the dosage form is disposed cushions the dosage form from impact when the package is dropped. The recesses of the package and the dosage forms disposed in the recesses may have essentially any shape. For example, the dosage forms may be disk-shaped tablets, oblong capsules or square-shaped pills. Similarly, shapes for recesses include circular, oblong, polygonal or star shapes in the plane of the blister sheet.

Furthermore, the walls and bottom of the recesses may define a shape in the form of a surface of revolution, about a vertical axis normal to the flange surrounding each of the recesses. For example, the recesses may have a curved, cup-like shape. Where the dosage forms are disc-shaped, they may each have an edge which contacts the walls of the recess in which each dosage form is disposed. The edge and walls define an annular region of contact coaxial with the vertical axis of the recess. The edge of such a disc-shaped dosage form may comprise a bevel which contacts the walls of the recess. The annular region of contact prevents shifting of the dosage form within the blister and the damage to the dosage form associated with such shifting.

By varying certain attributes of the various elements of blister packages according to the present invention, a package can be provided for a multitude of different uses. Utilizing different modes of attaching the lidding material sheet to the blister sheet, specifically, utilizing different adhesives in different amounts, may vary the difficulty required in peeling apart the two elements. Essentially, the stronger the adhesive and/or the more adhesive utilized, the harder it is to peel away the lidding material sheet. Similarly, varying certain dimensions of the blister packages may tailor the level of difficulty of grasping and bending. For instance, adjusting other dimensions tailors the amount of lidding material that is required to be pealed away to reveal the recess. Varying the thickness or type of the materials utilized in constructing both the blister sheet and lidding material sheet may also vary the difficulty in the bending operation, as well as the difficulty in peeling away the lidding material sheet. Certainly the type and thickness of these materials can have a significant effect on the ability to rip or chew through a package. While the blister package can include many different combinations of differing elements, three distinct embodiments are envisioned, a child proof design, an extremely child proof design, and an easy access design. The fact that all are possible from the same design speaks to the flexibility of the novel design of the present invention.

The child proof design requires a balance of the attributes of the elements just described and others such that the package is sufficiently difficult to open by children. Such a package is preferably useful for both frangible and non-frangible dosage forms, which are dangerous to children if ingested. The extremely child proof design requires a balance of the attributes of the elements such that the package is extremely difficult to open by a child. This extremely child proof design may also house frangible and non-frangible dosage forms, which are deadly to children if ingested. Such a package may prove more difficult for an adult also, but the danger of the dosage forms housed therein requires the heightened level of protection. Finally, the easy access design requires a balance of the attributes of the elements such that the package may be relatively easy to open. A package of this type may be useful in housing less dangerous or typical over the counter medications or vitamins.

As one of ordinary skill in the art will appreciate, the packaging in accordance with the present invention is highly versatile and is capable of being formatted such that it is child proof, extremely child proof or easily accessible. The materials and dimensions that can be used to construct these packages are highly dependent upon the overall objective. However, some general statements can be made regarding packaging design in accordance with the present invention. For example, all of the packages in accordance with the present invention should be blister packages having one or more blisters per card. Each blister package should, at least in a preferred embodiment, assist in reducing breakage during packaging, transport and storage. Each package will preferably be openable by peeling back the lidding layer based on exposure of a graspable edge of the lidding material accomplished by bending a portion of the package.

Furthermore, generally speaking, the greater the degree of child resistance desired, the greater the degree of distance for the placement of the recess relative to any one edge of the card. Also, the distance X between the edge of the recess and the closest portion of the unsealed area edge revealed during bending will be maximized. The more child resistant the package, generally the greater the thickness and/or ruggedness of the material(s) used in one or more of the layers. And also, generally the greater the degree of child resistance desired, the more aggressive the adhesive used. Of course, it may be possible to use very small amounts of a relatively aggressive adhesive and still provide an easily openable package in accordance with the present invention. Similarly, the use of a very thin polymer material layers, which is excessively rugged, resistant to bending, ripping and relatively impervious to a child's chewing, might be completely adequate, notwithstanding its relatively diminutive thickness. The distance X may also be relatively small when a particularly aggressive adhesive is used or when an easily openable blister package is desired. Indeed, by adjusting the variables discussed herein, it may be possible to use a relatively unagressive adhesive and yet provide a child resistant blister package. Thus, the package design according to the present invention is extremely versatile.

The packaging, according to different embodiment of the present invention can be rated as child resistant packages such as packages generally referred to in the industry as "F4", "F3", "F2" or "F1" packages. These monikers are given to packages that pass certain tests relating to how many children can gain access to the dosage forms housed in the packages in a certain amount of time. Typically, the number following the "F" refers to the number of tablets that would cause serious personal injury or serious illness to a twenty five pound child if ingested. For example, one such test begins with a base of fifty children, their goal being to access the dosage form housed in the package. The children are first given the packages without instructions to access the dosage forms. The children are given five minutes to attempt to gain access. After the five minutes expires, the children are asked to stop, at which point they are shown the proper steps to take in order to gain access to the dosage forms. Thereafter, the children are given an additional five minutes to work with the package. According to this one test, an F1 package would be one in which no more than five children can gain access to one pill during the ten minute period. A package would be given the F2 label if no more than five children can gain access to two pills. And, an F4 package would be one in which no more than five children can gain access to four pills in the ten minute period. While the above described test is one well known test utilized by the packaging industry, there are clearly many different tests that can be conducted in order to properly rate packages. These tests are generally done in accordance with 16 C.F.R. §1700.00-1700.20.

Certain embodiments according to the present invention may be rated as high as the well known industry standard known as "F1" packaging. For example, the extremely child proof embodiment discussed above would likely garner such an F1 rating. Other embodiments according to the present invention may be referred to by the also well know "F4" moniker. Finally, certain embodiments of the present invention may be referred to as F8 Plus or easy access. More particularly, the child proof design as discussed above would likely be rated as an F4 package, while the easy access design discussed above would likely be rated as an F8 plus package.

Of course, the robust and versatile design of the present invention allows the creation of tablet packages which are extremely child resistant and thus difficult for children to open, as well as packages which would be extremely easy for children to open. Which package is appropriate, however, is largely dependent upon the type of dosage form and active ingredient to be packaged thereby. Tablets containing, for example, symethacone, are relatively inert and the concern necessary for overdosing would be relatively small. On the other hand, opiates such as fentanyl may be extremely dangerous if not handled properly under a doctor's care and can be particularly dangerous to children. Accordingly, packages which are more child resistant would be appropriate.

DETAILED DESCRIPTION

A blister package 10 in accordance with an embodiment of the present invention is shown in FIGS. 1-5. Blister package 10 is configured so as to create a container for tablets that requires the bending of a portion of the elements of package 10 in order to gain access to the dosage forms contained therein. Blister package 10 preferably includes a blister sheet 12 and a sheet of lidding material 14. In various embodiments of the present invention, blister package 10 may be configured and dimensioned to allow for different levels of access to a dosage form contained therein, by varying the attributes of the various elements. This will be further discussed below.

Figure 1:
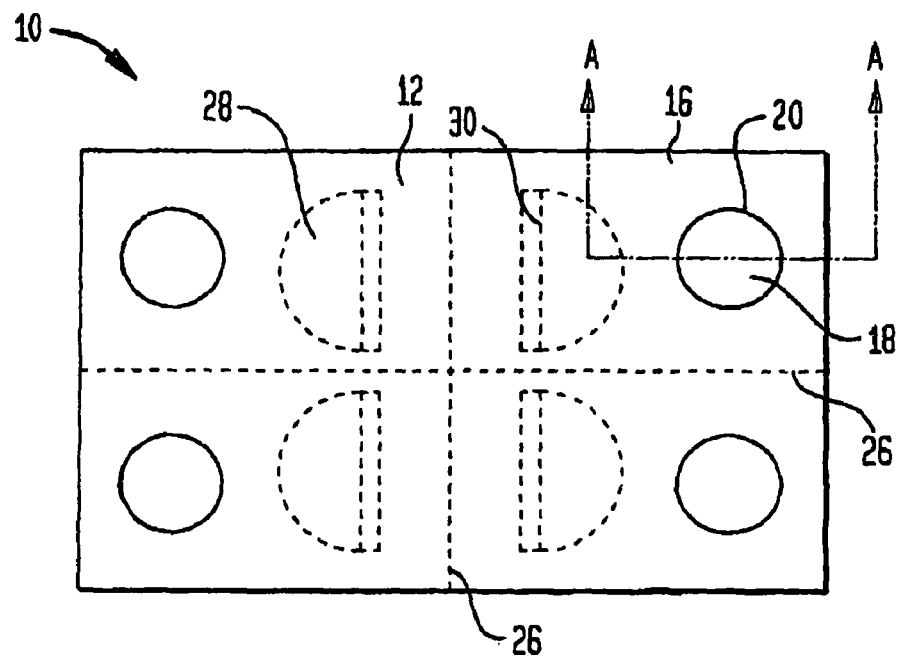
FIG. 1 is a bottom plan view of the blister package according to the present invention.
Figure 3:
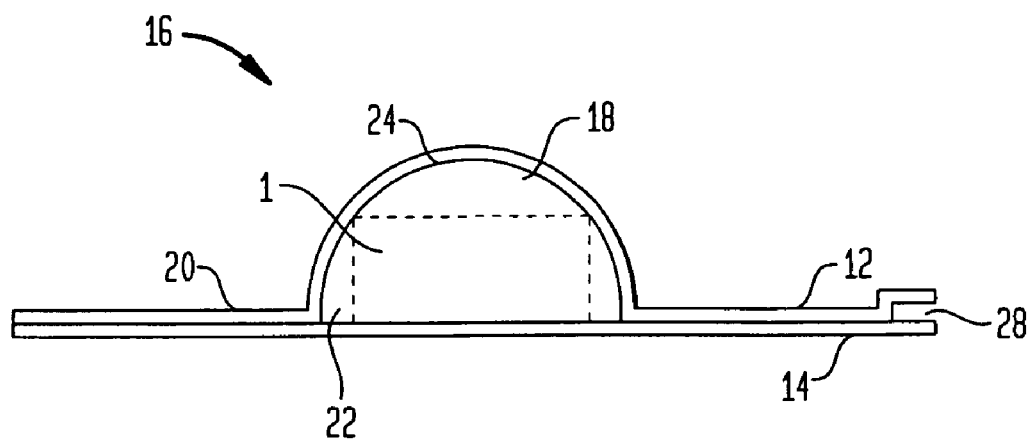
FIG. 3 is a cross-sectional side view of a unit package region of the blister package taken along line A-A of FIG. 1.

In a preferred embodiment of the present invention, as shown in FIG. 1, blister sheet 12 includes a plurality of unit package regions 16, such as the four regions shown in the figure. However, it is contemplated that a blister package 10 according to other embodiments of the present invention can include any number of unit package regions 16, including a single unit package region 16. Each unit package region 16 further includes a recess 18 and a flange 20 surrounding the recess. As best shown in FIG. 3, each recess 18 is dimensioned and configured to house a tablet or dosage form 1, and includes an open top 22 and a closed bottom 24. Recess 18 may be dimensioned or configured so as to house dosage forms 1 of varying sizes and/or shapes. In certain embodiments, recess 18 is circular (as shown in the figures) and has a diameter of one (1) inch or less. However, this diameter may be more preferably three quarters (¾) of an inch or less, or most preferably one half (½) of an inch or less. Similarly, recess 18 can vary in shape to house dosage forms of similar varying shapes. For example, recess 18 may be of an oblong shape to house pills of an oblong shape, although other shapes are contemplated, including polygonal or star shapes. Additionally, recess 18 may be configured to house more than one dosage form.

It is contemplated that the design of blister package 10 may also provide specific protection for frangible dosage forms by including recesses 18 that cooperate with such dosage forms to prevent shifting of the frangible dosage forms during transport and/or cushioning in the event of impact from the dropping of the package. Commonly assigned U.S. Pat. No. 6,155,423 to Katzner et al. ("the '423 patent"), the disclosure of which is hereby incorporated by reference herein, teaches one solution to this problem. The '423 patent discloses a blister package having a peelable layer which when pealed away allows for access to the dosage form. Therefore, the '423 patent provides a user accessibility to his or her frangible dosage form without the possibility of damaging the dosage form. The blister package of the '423 is also designed to help protect the tablet during storage, shipment and use. The present invention may utilize a similar design. For example, in certain embodiments, frangible or friable dosage forms may be disposed in each recess 18 of blister sheet 12 such that the dosage forms engage the walls of each recess 18, and the walls hold dosage form 1 away from closed bottom 24 and adjacent lidding material 14. Such a configuration is best shown in FIG. 3. This design also protects any dosage form housed therein from damage by preventing shifting of the dosage form during transport or other movement typically imparted by a user. For example, an empty space between each dosage form and closed bottom 24 cushions the dosage form from impact if and when package 10 is dropped or otherwise jarred.

Furthermore, the walls and closed bottom 24 of recess 18 may define a shape in the form of a surface of revolution, about a vertical axis normal to flange 20 surrounding each of the recesses 18. For example, recesses 18 may have a curved, cup-like shape. Where the dosage forms are disc-shaped, they may each have an edge which contacts the walls of recess 18 in which each dosage form is disposed. The edge and walls preferably define an annular region of contact coaxial with the vertical axis of recess 18. The edge of such a disc-shaped dosage form may comprise a bevel which contacts the walls of recess 18. The annular region of contact prevents shifting of the dosage form within the blister and the damage to the dosage form associated with such shifting.

Figure 2:
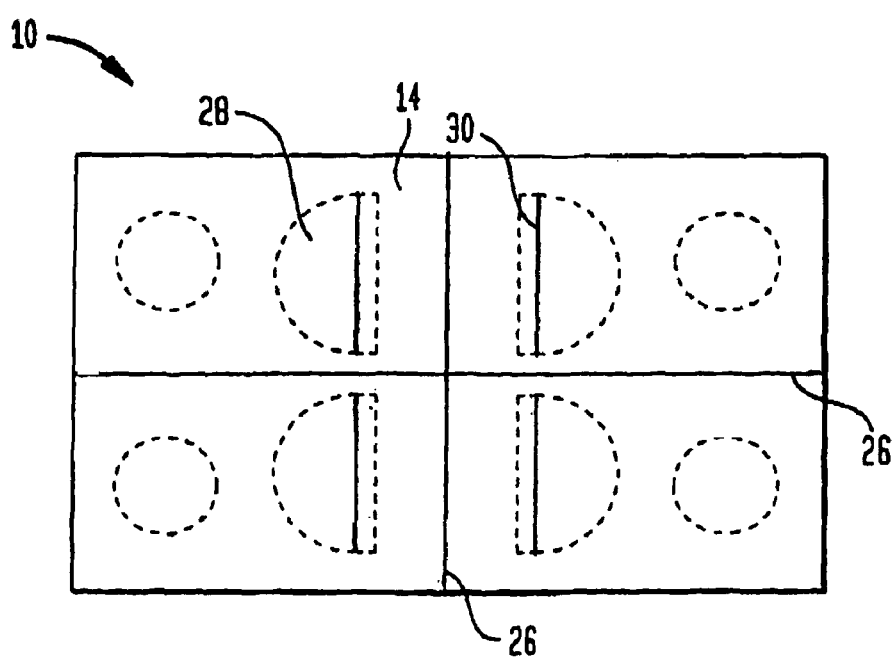
FIG. 2 is a top plan view of the blister package of FIG. 1.

Lidding material sheet 14 (best shown in FIG. 2) is preferably a unitary sheet that overlies recesses 18 and is peelably attached to flanges 20, thereby covering any dosage forms 1 housed within recesses 18. As best shown in FIG. 2, lidding material sheet 14 includes lines of weakness 26. Essentially, lines of weakness 26 are lines of holes, scores or perforations through lidding material 14 that allow the lidding material to be more easily torn away. It should be noted that lines of weakness 26 may extend through lidding material sheet 14 and blister sheet 12, as shown in the FIGS. In embodiments that include such a configuration, unit package regions 16 may be removed from other unit package regions. In fact, lines of weakness 26 in these embodiments define the size and shape of unit package regions 16. It should also be noted that providing lidding material sheet 14 with lines of weakness 26 may, in certain manufacturing processes, cause such to extend through blister sheet 12.

Figure 4:
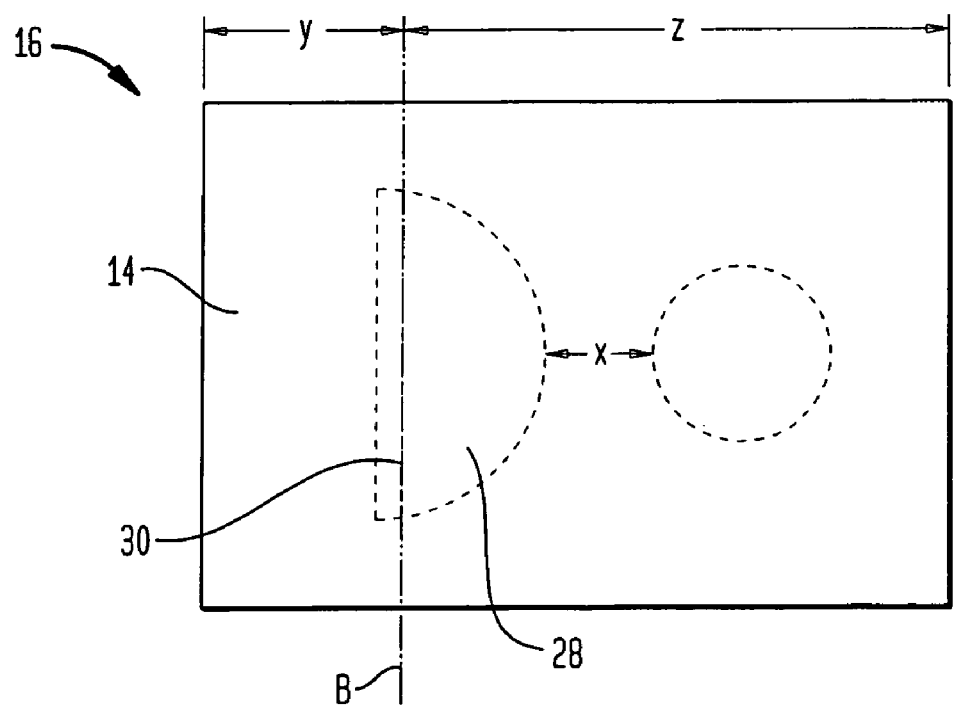
FIG. 4 is top plan view of a unit package region of the blister package of FIG. 1.

According to the present invention, lidding material sheet 14 is preferably glued to blister sheet 12. However, other modes of attaching lidding material sheet 14 to blister sheet 12 are contemplated, such as heat sealing, RF sealing and the like. While lidding material sheet 14 is substantially connected to blister sheet 12, there exists unconnected, unsealed or unglued areas 28. These areas (shown in the FIGS. with phantom lines) are essentially areas where blister sheet 12 is not glued or otherwise attached to lidding material sheet 14. This, of course, is in addition to the inserted areas defined by the recesses. As shown in FIGS. 1, 2 and 4, unsealed areas 28 are specifically shaped to allow both easy access by a user and easy tearing away of lidding material sheet 14 from blister sheet 12. For example, the shape of unsealed areas 28 as shown in the FIGS. 1-5 is such that the thumb and forefinger of a user can easily grasp lidding material 14. However, it is contemplated that unsealed areas 28 may be of any shape including, but not limited to, circular, semi circular, triangular, squared shaped, or other polygons. Perforations 30 preferably extend along at least a portion of unsealed areas 28. Perforations 30 are essentially a shorter version of lines of weakness 26, which do not extend to any of the edges of unit package regions 16. This important because such a configuration reduces the tearing of any portion of a given unit package region 16 and retards access without bonding. Thus, the only way unsealed areas 28 can be accessed is by the bending method discussed below. Once again, as mentioned above in the discussion on lines of weakness 26, perforations 30 may extend through both lidding material sheet 14 and blister sheet 12. However, once again, the particular configuration depends upon the manufacturing process. It is also contemplated that perforations 30 may be constructed so as to be deeper or shallower in different embodiments. This may allow for different accessing conditions as will be discussed further below. In addition, perforations 30 are preferably formed such that lidding material sheet 14 remains flat sided. In other words, a user is preferably unable to grasp an edge created by perforations 30 or any other part of lidding material sheet 14. This, in turn, prevents the removal of lidding material sheet 14 from blister sheet 12, absent the performance of other steps which will be discussed below.

Figure 5:
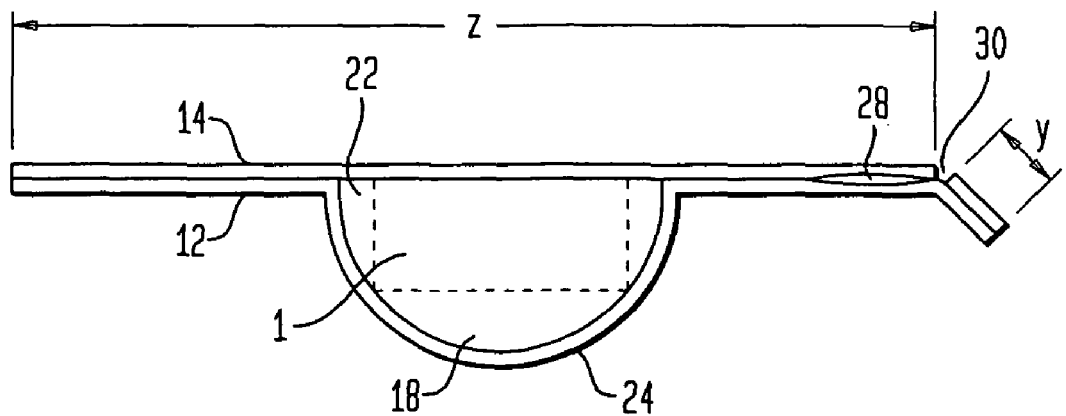
FIG. 5 is a cross-sectional side view of a unit package region with a section bent about an axis B to allow for peeling of a lidding material from a blister sheet.

As best shown in FIGS. 4 and 5, blister package 10 must be bent along an axis B in order for unglued areas 28 to be accessed by a user. Axis B is preferably an axis extending along the line of perforations 30. Upon bending, blister package 10 may be separated into two separate portions, Y and Z, residing on either side of axis B. In operation, a user grasps portions Y and Z in either hand and bends them towards one another so as to split lidding material sheet 14 along perforations 30. It is noted that blister package 10 should be bent so that lidding material sheet 14 remains on the outside of the bend. This bent state, with a split lidding material sheet 14, is best shown in FIG. 5. Given the fact that perforations 30 are formed through lidding material sheet 14 along a portion which is at least partially unsealed, the splitting of lidding material sheet 14 along perforations 30 allows for a user to then access or grasp unsealed area 28. As shown in FIG. 5, a user can quite easily grasp at least a portion of unsealed area 28 when perforations 30 are split. Essentially, the bending of blister package 10 causes lidding material sheet 14 to move into a non-flat sided state, or one in which a user is able to grasp a portion of the lidding material adjacent unsealed area 28 in the proximity of axis 13. Thereafter, the user can peal away the portion of lidding material sheet 14 that resides in portion Z, which, in turn, exposes recess 18. Therefore, dosage form 1 can be easily removed. The effort required in peeling away lidding material sheet 14 depends upon, amongst other things, the mode of attachment of lidding material sheet 14 to blister sheet 12, the thickness and rigidity of the blister sheet 12 and or lidding sheet 14, the size at the unsealed area 28, the amount of space one has to grasp the package (portion Y) and the distance that the lidding sheet 14 must be pulled to provide access to the recess.

Figure 6:
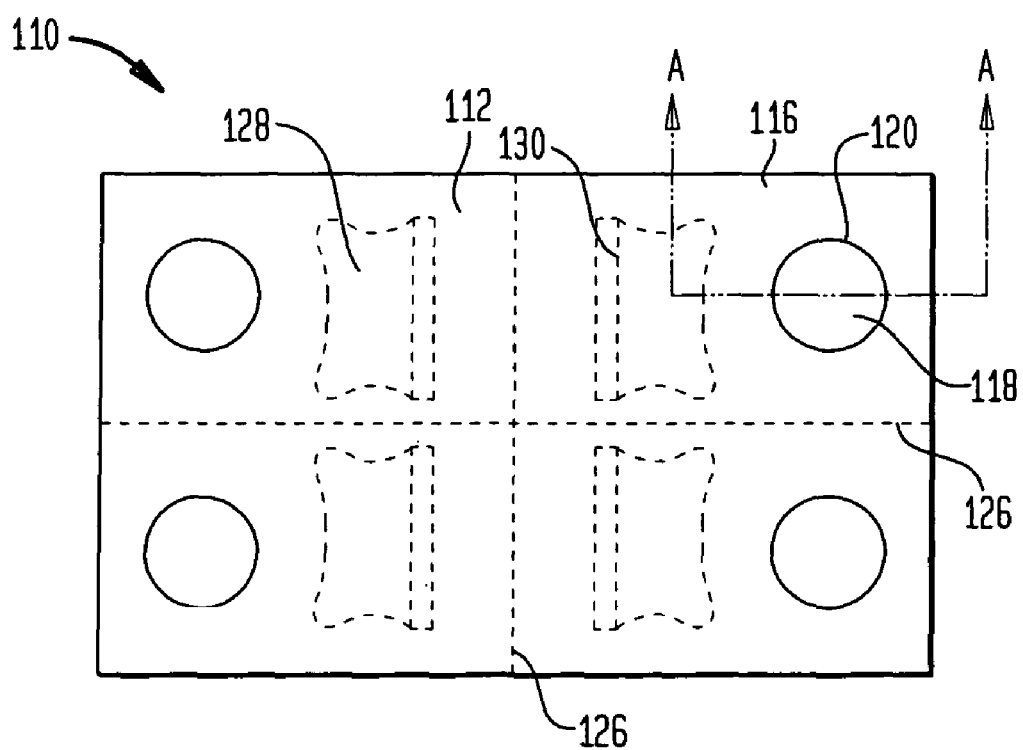
FIG. 6 is a bottom plan view of the blister package according to another embodiment of the present invention.
Figure 7:
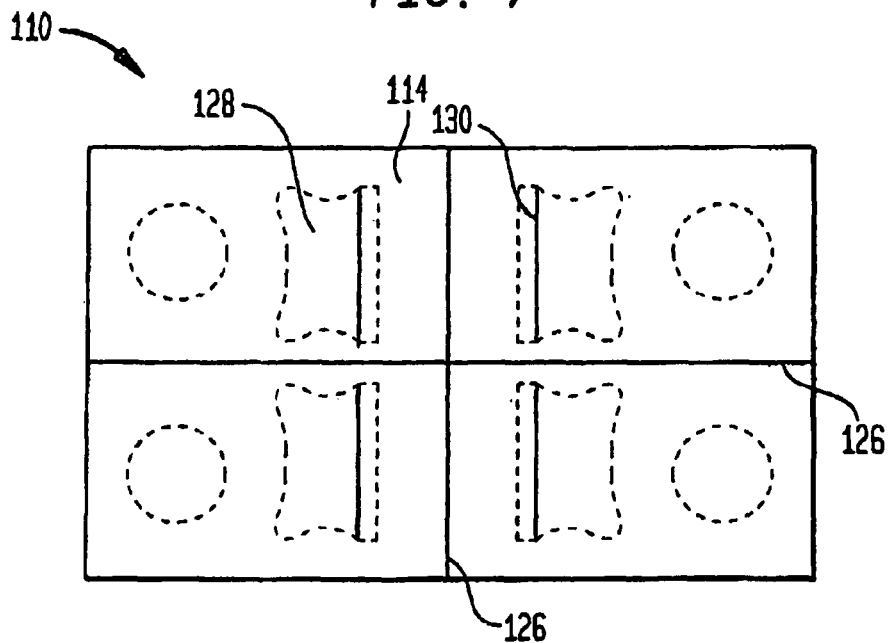
FIG. 7 is a top plan view of the blister package of FIG. 6.
Figure 8:
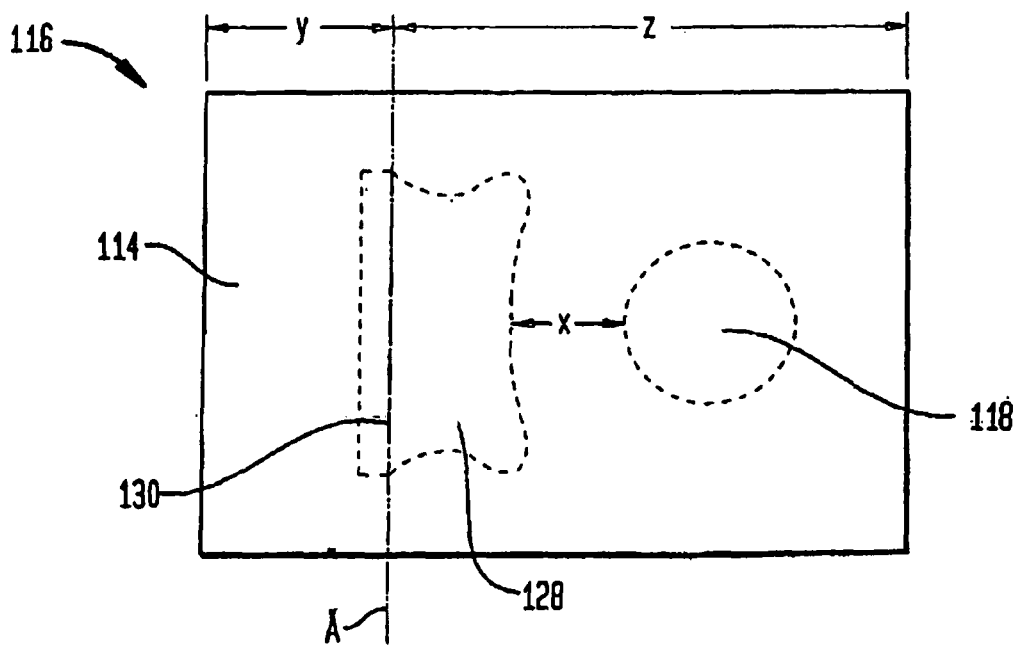
FIG. 8 is top plan view of a unit package region of the blister package of FIG. 6.

FIGS. 6-8 depict an additional embodiment according to the present invention that is a blister package 110 having a differently shaped unsealed or unglued area 128. The shape of unsealed areas 128 as shown in FIGS. 6-8 is such that the thumb and forefinger of a user can more easily grasp lidding material 14, and subsequent tearing of lidding material 14 away from blister sheet 12 is guided to uncover the entirety of recess 18. These guiding unsealed areas 128 allow for a more uniform tear to be made over and around recess 118. The construction and operation of blister package 110 is preferably similar to the above described package 10, except for the guiding unsealed areas 128.

It has been discovered that varying certain attributes of the various elements of blister package 10 may provide for different types and different levels of functionality. For example, utilizing different modes of attaching lidding material sheet 14 to blister sheet 12, specifically, utilizing different amounts of different adhesives, may vary the difficulty required in peeling apart the two elements. As one example, the stronger the adhesive utilized, the harder it is to peel away lidding material sheet 14 from blister sheet 12. Conversely, using relatively little of even a strong adhesive may prove useful for an easy access application. Varying the length of portions Y and Z may also determine the level of difficulty of accessing dosage form 1. For example, varying the length of portions Y and Z may make the bending operation more or less difficult, by providing smaller or larger portions for a user to manipulate. A thick layer of a rigid material could also make it difficult to bend blister package 10 so as to reveal the unsealed area 28. When combined with a relatively short Y, providing little room to grip may make it difficult to bend portion Y and provide access. Similarly, recess 18 may be situated at a varying distance X (shown in FIGS. 4 and 5) from unsealed area 28. The greater the distance X, the relatively more difficult it is to peal away lidding material sheet 14 depending, of course, on the type of adhesive and the amount of adhesive used. Finally, varying the thickness or type of the materials utilized in constructing both blister sheet 12 and lidding material sheet may also vary the difficulty in the bending operation, as well as the difficulty in peeling away lidding material sheet 14. As one will appreciate, many of the possible ways to construct the packages of the invention depend upon the use contemplated and the interdependence of a number of elements as discussed herein.

While blister package 10 can include many different combinations of differing elements, three distinct embodiments will be discussed further below. Each of the embodiments may be configured to house frangible or non-frangible dosage forms. It is contemplated that varying any or all of the above discussed attributes may provide a blister package in accordance with any of these embodiments. In other words, it is possible to achieve a blister package that adheres to a specific embodiment by providing different combinations of element attributes.

The first embodiment that will be discussed can best be described as a child proof design that may be utilized with any type of dosage form. Such a design might be, for example, known in the art as an F4 package, as discussed above. In this embodiment the length of portion Y may be decreased, while at the same time increasing the length of portion Z. Shortening the length of portion Y with respect to portion Z makes it more difficult to manipulate blister package 10 to perform the aforementioned bending step, thus making it more difficult to split the lidding material along perforations 30 and ultimately accessing dosage form 1. The lengthening of portion Z may allow for the increase of distance X. This necessarily also increases the difficulty in removing lidding material 14 to access dosage form 1. Essentially, the farther away unglued area 28 is from recess 18, the more difficult it is to peal away lidding material sheet 14. Lengthening of portion Z also allows for recess 18 to be situated a greater distance from the various edges of blister package 10. Thus, making the package less susceptible to improper access of dosage form 1, such as by biting, tearing or ripping.

In accordance with this embodiment, it is also contemplated, in addition to varying the lengths of portions Y and Z, that the mode of attachment of lidding material sheet 14 to blister sheet 12, the materials and the thickness of the materials utilized in blister package 10 may also be varied. For example, stronger adhesive may be utilized to increase the effort required in peeling away lidding material sheet 14. One such adhesive is an adhesive supplied by Alcan Pharma Center of Shelbyville, Ky. ("Alcan") under the number 4563 and may be utilized to create such an F4 package according to this embodiment. Similarly, utilizing thicker or stronger materials may increase the difficulty in bending blister package 10. The thicker or stronger materials are also more resistant to biting, chewing, tearing and the like.

While, there are indeed many different combinations that may provide a blister package in accordance with this first embodiment, certain preferred embodiments are envisioned. Once again however, in accordance with this embodiment, it is contemplated that varying any of the attributes in order to make accessing dosage form 1 more difficult, may allow for other attributes to be varied in order to make accessing dosage form 1 easier. In other words, blister packages in accordance with this first embodiment are achieved through a balance of the different attributes. For example, if distance X is increased, a weaker adhesive may be utilized while still providing a blister package in accordance with this embodiment.

The second embodiment that will be discussed can best be described as an extremely child proof design that is specially suited for housing highly dangerous dosage forms (e.g. F1). Designs in accordance with this embodiment should comply with standards set for other extremely child proof packages. For example, packages according to this embodiment should prevent a certain amount of children from accessing the dosage forms contained therein, in a certain amount of time, as per the previously discussed F1 rating testing. In this second embodiment, like in the first embodiment, the length of portion Y may be decreased, while at the same time increasing the length of portion Z. Once again, shortening the length of portion Y with respect to portion Z makes it more difficult to manipulate blister package 10 to perform the bending step of blister package 10 and the lengthening of portion Z may increase distance X and the situation of recess 18 from the edges of unit package region 16. In this embodiment, the length of portion Y should be decreased so as to make it extremely difficult to manipulate blister package 10, and the length of portion Z should be increased so as to make it extremely difficult to peal away lidding material sheet 14. Like that of the first embodiment, both the mode of attachment of lidding material sheet 14 to blister sheet 12 and the materials and thicknesses of materials utilized in blister package 10 may also be varied. Stronger adhesive should be utilized to increase the effort required in peeling away lidding material sheet 14, and thicker or stronger materials should be utilized to increase the difficulty in bending blister package 10.

While, there are indeed many different combinations that may provide a blister package that is extremely child proof, a preferred embodiment is envisioned. For example, an extremely child proof embodiment of blister package 10 may include an overall length of approximately four (4) inches, and most preferably of 4.095 inches, and an overall width of approximately two and a half (2.5) inches, and most preferably of 2.577 inches, as well as a portion Y having a length of about 10 mm, a portion Z having a length of about 42 mm, and a distance X having a length of about 10.3 mm. In this preferred embodiment, blister sheet 12 may be constructed of material supplied by Alcan and offered as PCS technical and material specification no. 92011 ("the 92011 material) having a thickness of approximately 205 μm. The 92011 material includes several different individual layers, for example, approximately 60 μm of PVC film, approximately 25 μm of polyamide film, approximately 60 μm of aluminum foil and approximately 60 μm of additional PVC film, which are preferably at least joined together by suitable adhesives. Lidding material sheet 14, on the other hand, may be constructed of PCS technical and material specification nos. 15144 having a thickness of approximately 37 μm or 15127 having a thickness of approximately 37 μm. Both of these materials are also supplied by Alcan, and preferably include a paper layer, an approximately 12 μm thick polyester film, an approximately 25 μm thick aluminum foil layer and a heat seal coating. In addition, this embodiment may utilize adhesive also supplied by Alcan under the number 4516 for attaching lidding material sheet 14 to blister sheet 12. Once again, blister packages in accordance with this extremely child proof embodiment are achieved through a balance of the different attributes. While these specifics are provided for a single preferred embodiment, it is noted that other materials or dimensions may be utilized. For example, the selection of adhesive for use with this second embodiment may be chosen by selecting an adhesive that provides a connection strength that does not fall below 454 g/in., as per an ASTM F88 test method. In one instance, use of the identical materials and construction, and replacement of adhesive 4516 with adhesive 4563 (also supplied by Alcan) provided an "F4" package while the use of adhesive 4516 provided an "F1" package.

Conversely, a third embodiment can be designed for easy access or easy peel (e.g., for packaging designed to house less dangerous dosage forms). For example, such a package may be considered an F8 plus package, as further discussed above. A blister package in accordance with this third embodiment may be useful in housing over the counter medications and/or vitamins. In this third embodiment, the length of portion Y may be increased, while at the same time decreasing the length of portion Z. Unlike the previously discussed embodiments, the lengthening of portion Y with respect to portion Z makes it easier to manipulate blister package 10 and the shortening of portion Z may allow for the decrease of distance X, thus lessening the difficulty in removing lidding material 14 to access dosage form 1. Also in this embodiment, the length of portion Y should be decreased and the length of portion Z should be decreased so as to make it relatively easy to bend blister package 10 and to peal away lidding material sheet 14, by all persons. Like that of the first and second embodiments, both the mode of attachment of lidding material sheet 14 to blister sheet 12 and the materials and material thicknesses utilized in blister package 10 may also be varied. In addition, in this embodiment, weaker adhesive may be utilized to decrease the effort required in peeling away lidding material sheet 14, and weaker or thinner materials may be utilized to decrease the difficulty in bending blister package 10.

While, there are indeed many different combinations that may provide a blister package that is designed for easy access, a preferred embodiment is envisioned. In this embodiment, providing weaker attributes is key. The package should have an overall user-friendly design that provides for easy use. For example, such a user-friendly package could employ unsealed covers like those depicted in the embodiment of FIGS. 6-8, and referred to as elements 128. Once again, the attributes may be varied such that decreasing the difficulty provided by certain attributes may allow for the increase in difficulty provided by others. For instance, a blister package in accordance with this embodiment may utilize an extremely weak adhesive. For this type of package, the material or thickness of material may not need to be weaker or decreased all that much.

It is contemplated that, in addition to the above discussed attributes, other attributes of other elements of blister package 10, and blister package 110, can be varied to provide differing packages. For example, unsealed areas 28, 128 may be configured and/or sized to provide a more difficult or easier grasping by a user. Similarly, perforations 30, 130 may be designed such that splitting of the lidding material is a more difficult or easier task. Nonetheless, blister package 10 provides an extraordinarily functional package design for housing all sorts of dosage forms or pills.

Finally, one preferred formation method of the aforementioned blister packages 10, 110 and the packaging process of dosages forms 1 therein will be described. It is to be understood that many different suitable processes may be utilized in accordance with the present invention, and the following is but one preferred method. In such a method/process, sheets of material for forming blister sheet 12 and lidding material 14 are preferably received in roll form and fed or loaded onto a blister machine. It is noted that such machines are well-known in the art. The material forming blister sheet 12 is then preferably moved to a forming station where recesses 18 are formed into the material by tools such as forming plugs. Tablets 1 are then preferably placed into each open recess 18 of blister sheet 12.

With recesses 18 each containing one or more tablets 1, blister sheet 12 is then preferably moved to a sealing station where upper and lower sealing plates may be utilized to seal lidding material 14 to blister sheet 12. The aforementioned sealing plates preferably utilize heat and pressure over the course of a certain dwell time (cycles/speed) to heat a suitable adhesive (like those described above) to seal lidding material 14 to blister sheet 12. Subsequent to this sealing step, desired perforations may be formed in the package, and individual blister cards 10 (with multiple recesses 18) may be punched out. It is noted that the formed perforations may be useful in this punch out procedure, but may also remain in the final blister package 10 as discussed above. Ultimately, the individual packages 10 are preferably delivered to final packaging stations via conveyors or the like.

The dosage forms, usually tablets, which can be packaged using the present invention are not at all limited by the type of tablet or the type of active pharmaceutical ingredient ("API") used therein. These API's include, without limitation, analgesics, anti-inflammatories, antipyretics, antibiotics, antimicrobials, anxiolytics, laxatives, anorexics, antihistamines, antidepressants, antiasthmatics, antidiuretics, antiflatuents, antimigraine agents, antispasmodics, sedatives, antihyperactives, antihypertensives, tranquilizers, decongestants, beta blockers, peptides, proteins, oligonucleotides and other substances of biological origin, and combinations thereof. Also contemplated are the drugs and pharmaceutically active ingredients described in Mantelle, U.S. Pat. No. 5,234,957, in columns 18 through 21. That text of Mantelle is hereby incorporated by reference. Any of the forgoing API's can be used in the form of any salt, hydrate, solvate, polymorph, or individual optical isomer, and any mixture thereof.

In particular, opiates, drugs used to treat pain, drugs used in psychiatry or in the treatment of schizophrenia, such as clozapine and cytotoxic substances are particularly preferred. Also preferred is any API which is intended to treat the elderly or any API which requires the use of a child-proof package, and more particularly an "F1" package.

Legal opiates which may be packaged according to the invention include prescription drugs such as, without limitation, alfentanil, alphaprodine, anileridine, benzylmorphine, bezitramide, buprenorphine, butorphanol, clonitazene, codeine, codeine phosphate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone, metopon, morphine, morphine hydrochloride, morphine sulfate, myrophine, nalbuphine, narceien, nicomorphine, norlevorphanol, normethadone, normorphine, norpipanone, opium, oxycodone, oxymorphone, papveretum, pentazocine, phenadoxone, phenazocine, phenoperidine, piminodine, piritramide, proheptazine, promedol, propirm, propoxyphene, remifentanil, sufentanil and tilidine. The class of compounds generally known as opiates also includes illicit drugs such as heroin and cocaine. Opiates in accordance with the present invention include those identified above as well as any listed as controlled substances pursuant to 21 C.F.R. §1308.12. Opiates are given to patients for a variety of reasons, most frequently for pain mitigation of one type or another.

A cytotoxic substance includes any agent that kills cells. These substances are generally used in the treatment of malignant and other diseases. They are designed to destroy rapidly growing cancer cells. They have been shown to be mutagenic, carcinogenic and/or teratogenic, either in treatment doses or animal and bacterial assays. Cytotoxic drugs that interfere with critical cellular processes including DNA, RNA, and protein synthesis, have been conjugated to antibodies and subsequently used for in vivo therapy. Such drugs, include, but are not limited to:

i) intercalating agents, in particular doxorubicin (Adriamycin), daunorubicin, epirubicin, idarubicin, zorubicin, aclarubicin, pirarubicin, acridine, mitoxanthrone, actinomycin D, eptilinium acetate;

ii) alkylating agents chosen from platinum derivatives (cisplatin, carboplatin, oxaliplatin);

iii) a compound chosen from the other groups of alkylating agents: cyclophosphamide, ifosfamide, chlormetrine, melphalan, chlorambucil, estramustine, busulfan, mitomycin C, nitrosoureas: BCNU (carmustine), CCNU (lomustine), fotemustine, streptozotocin, triazines or derivatives: procarbazine, dacarbazine, pipobroman, ethyleneimines: altretamine, triethylene-thio-phosphoramide, iv) a compound chosen from the other groups of antimetabolic agents: antifolic agents: methotrexate, raltitrexed, antipyrimidine agents: 5-fluorouracil (5-FU), cytarabine (Ara-C), hydroxyurea antipurine agents: purinethol, thioguanine, pentostatin, cladribine, cytotoxic nucleoside synthesis inducers: gemcitabine, v) a compound chosen from the other groups of tubulin-affinity agents, vinca alkaloids which disrupt the mitotic spindle: vincristine, vinblastine, vindesine, navelbine, agents which block the depolymerization of the mitotic spindle: paclitaxel, docetaxel, agents which induce DNA cleavage by inhibition of topoisomerase II: etoposide, teniposide, topoisomerase I inhibitors which induce DNA cleavage: topotecan, irinotecan, vi) a DNA splitting or fragmenting agent, such as bleomycin, vii) one of the following compounds: plicamycin, L-asparaginase, mitoguazone, dacarbazine, viii) an anticancer progestative steroid; medroxy-progesterone, megestrol, ix) an anticancer estrogen steroid: diethylstilbestrol; tetrasodium fosfestrol, x) an antiestrogen agent: tamoxifen, droloxifen, raloxifen, aminoglutethimide, xi) a steroidal antiandrogenic agent (eg cyproterone) or a non-steroidal antiandrogenic agent (flutamide, nilutamide).

In addition to the API's mentioned herein, the dosage forms of the invention can, in addition or instead, include vitamins, minerals and dietary supplements. As used in this disclosure, the term "vitamin" refers to trace organic substances that are required in the diet. For the purposes of the present invention, the term "vitamin(s)" includes, without limitation, thiamine, riboflavin, nicotinic acid, pantothenic acid, pyridoxine, biotin, folic acid, vitamin B.sub.12, lipoic acid, ascorbic acid, vitamin A, vitamin D, vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMM), flavin adenine dinucleotide (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B.sub.12, lipoyllysine, 11-cis-retinal, and 1,25-dihydroxycholecalciferol. The term "vitamin(s)" also includes choline, carnitine, and alpha, beta, and gamma carotenes.

The term "mineral" refers to inorganic substances, metals, and the like required in the human diet. Thus, the term "mineral" as used herein includes, without limitation, calcium, (calcium carbonate), iron, zinc, selenium, copper, iodine, magnesium, phosphorus, chromium and the like, and mixtures thereof. The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

In general, the amount of active ingredient incorporated in each tablet or dosage form (API, vitamin, mineral, dietary supplement and the like), may be selected according to known principles of pharmacy. An effective amount of API is specifically contemplated. By the term "effective amount," it is understood that, with respect, to for example, a "pharmaceutically effective amount" is contemplated. A "pharmaceutically effective amount" is the amount or quantity of a drug or API which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The amount of active ingredient used can vary greatly. Of course, the size of the dosage form, the requirements of other ingredients, and the number of, for example, tablets which constitute a single dose will all impact the upper limit on the amount of pharmacologically active ingredient which can be used. However, generally, the active ingredient is provided in an amount of between greater than zero and about 80% by weight of the finished tablet and, more preferably, in a range of between greater than zero and about 60% by weight thereof. Put in other terms, the active ingredient can be included in an amount of between about 1 microgram to about 2 grams, and more preferably between about 0.01 and about 1000 milligrams per dosage form, i.e., per tablet.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A blister package comprising:
 a unitary blister sheet defining a plurality of unit package regions, each unit package region including a recess having an open top and a flange surrounding the recess; and
 a unitary sheet of lidding material peelably sealed to the flange, wherein (i) said blister sheet and said sheet of lidding material further define unsealed areas for facilitating peeling of said lidding material from said blister sheet, (ii) each said unsealed area being disposed apart from a border of a respective unit package region, (iii) each said unsealed area covered by the lidding material wherein the lidding material over each unsealed area consists of a straight line of weakness that does not extend to the edges of the unit package region, and wherein bending the straight line of weakness breaks the lidding material and leaves the blister sheet intact, and (iv) each said unsealed area is directly accessible by a user upon the bending of at least a portion of said blister sheet and said sheet of lidding material along an axis that extends along the straight line of weakness in the lidding material.

2. The blister package according to claim 1, wherein said blister sheet includes four unit package regions.

3. The blister package according to claim 2, wherein each unit package region is removable from said blister package.

4. The blister package according to claim 3, further including additional lines of weakness, wherein each unit package region is defined by the additional lines of weakness.

5. The blister package according to claim 1, wherein said straight line of weakness comprise perforations for accessing the unsealed areas.

6. The blister package according to claim 1, wherein the recess includes walls and a closed bottom.

7. The blister package according to claim 6, wherein a dosage form may be disposed in the recess so that the walls hold the dosage form away from the closed bottom and adjacent said lidding material so that there is an empty space between each dosage form and the closed bottom of the recess.

8. A packaged dosage form including a package as claimed in claim 1 and a pharmaceutical dosage form disposed in the recess.

9. The packaged dosage form claimed in claim 8, wherein the pharmaceutical dosage form is fentanyl.

10. A method of removing a dosage form from a blister package, the method comprising:
   providing said blister package having a blister sheet and a sheet of lidding material, wherein the blister sheet and the sheet of lidding material define a plurality of unit package regions, each unit package region including at least one recess and at least one unsealed area disposed apart from a border of the unit package region, the unsealed area being covered by the lidding material wherein the lidding material over each unsealed area consists of a straight line of weakness, wherein bending the straight line of weakness breaks the lidding material and leaves the blister sheet intact, and wherein the straight line of weakness does not extend to any of the edges of the unit package region;
   bending at least a portion of said blister package to allow direct access to the unsealed area;
   grasping at least a portion of the lidding material corresponding to the unsealed area;
   peeling away the portion of the lidding material to reveal at least one dosage form disposed in the recess; and
   removing the at least one dosage form.

11. The method according to claim 10, further comprising the step of separating at least one unit package region from other unit package regions.

12. The method according to claim 10, wherein said bending step includes splitting a portion of the lidding material along the straight line of weakness.

13. A blister package comprising:
   a blister sheet defining at least one unit package region, said unit package region including at least one recess having an open top and a flange surrounding the recess; and
   a sheet of lidding material including a straight line of perforations in each of said unit package region, said sheet of lidding material peelably sealed to the blister sheet and defining at least one unsealed area between said blister sheet and said sheet of lidding material, wherein the lidding material over each unsealed area consists of the straight line of perforations,
   wherein (i) the unsealed area is disposed apart from a border of the at least one unit package region, (ii) the straight line of perforations are located along only a single edge of the at least one unsealed area, and do not extend to any of the edges of the unit package region, and (iii) bending of said blister package along the straight line of perforations in the lidding material allows for splitting of the straight line of perforations in the lidding material while leaving the blister sheet intact and direct access of the at least one unsealed area.

14. The blister package according to claim 13, wherein said blister sheet includes a plurality of unit package regions, each unit package region including at least one recess and at least one flange surrounding the at least one recess.

15. The blister package according to claim 13, wherein the at least one recess includes walls and a closed bottom.

16. The blister package according to claim 15, wherein a dosage form may be disposed in the recess so that the walls hold the dosage form away from the closed bottom and adjacent said lidding material so that there is an empty space between each dosage form and the closed bottom of the recess.

17. The blister package according to claim 7, wherein the walls are sloped and wherein the dosage form further comprises a beveled edge.

18. The blister package according to claim 16, wherein the walls are sloped and wherein the dosage form further comprises a beveled edge.

* * * * *